United States Patent
Neidert et al.

(10) Patent No.: US 10,959,669 B2
(45) Date of Patent: Mar. 30, 2021

(54) SYSTEMS AND METHODS FOR ASSESSING THE EFFICACY OF NEUROMODULATION THERAPY

(71) Applicant: Medtronic Ardian Luxembourg S.a.r.l., Luxembourg (LU)

(72) Inventors: Michael Neidert, San Francisco, CA (US); Paul Coates, Corte Madera, CA (US); Robert L. Melder, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 42 days.

(21) Appl. No.: 16/250,234

(22) Filed: Jan. 17, 2019

(65) Prior Publication Data
US 2019/0223785 A1  Jul. 25, 2019

Related U.S. Application Data

(60) Provisional application No. 62/621,285, filed on Jan. 24, 2018.

(51) Int. Cl.
*A61B 5/00* (2006.01)
*G16H 40/63* (2018.01)
(Continued)

(52) U.S. Cl.
CPC .......... *A61B 5/4836* (2013.01); *A61B 5/0538* (2013.01); *A61B 5/1076* (2013.01);
(Continued)

(58) Field of Classification Search
CPC ............ A61N 1/37516; A61N 1/36007; A61N 1/36057; A61N 1/36117; A61B 5/4836;
(Continued)

(56) References Cited

U.S. PATENT DOCUMENTS

| | | |
|---|---|---|
| 4,602,624 A | 7/1986 | Naples et al. |
| 4,649,936 A | 3/1987 | Ungar et al. |

(Continued)

FOREIGN PATENT DOCUMENTS

| | | |
|---|---|---|
| EP | 2457615 | 12/2014 |
| EP | 2934357 | 11/2017 |

(Continued)

OTHER PUBLICATIONS

International Searching Authority, International Search Report and Written Opinion for International Application No. PCT/US2019/014360, dated Apr. 24, 2019, 16 pages.

(Continued)

*Primary Examiner* — Michael W Kahelin
*Assistant Examiner* — George E Banis

(57) ABSTRACT

Systems and methods for performing and assessing neuromodulation therapy are disclosed herein. One method for assessing the efficacy of neuromodulation therapy includes positioning a neuromodulation catheter at a target site within a renal blood vessel of a human patient and delivering neuromodulation energy at the target site with the neuromodulation catheter. The method can further include obtaining a measurement related to a dimension of the renal blood vessel via a sensing element of the neuromodulation catheter. The measurement can be compared to a baseline measurement related to the dimension of the renal blood vessel to assess the efficacy of the neuromodulation therapy. In some embodiments, the baseline measurement is obtained via the sensing element of the neuromodulation catheter prior to delivering the neuromodulation energy.

18 Claims, 8 Drawing Sheets

(51) Int. Cl.

| | |
|---|---|
| A61B 5/11 | (2006.01) |
| A61B 5/0205 | (2006.01) |
| A61B 5/021 | (2006.01) |
| A61B 5/024 | (2006.01) |
| A61N 1/36 | (2006.01) |
| A61N 1/375 | (2006.01) |
| A61B 18/14 | (2006.01) |
| A61B 5/107 | (2006.01) |
| A61B 18/24 | (2006.01) |
| A61B 5/0538 | (2021.01) |
| A61B 18/18 | (2006.01) |
| A61B 18/00 | (2006.01) |
| A61B 5/0522 | (2021.01) |

(52) U.S. Cl.
CPC ........ *A61B 5/6857* (2013.01); *A61B 18/1492* (2013.01); *A61B 18/1815* (2013.01); *A61B 18/24* (2013.01); *A61N 1/36007* (2013.01); *A61N 1/36057* (2013.01); *A61N 1/36117* (2013.01); *A61N 1/37516* (2017.08); *A61B 5/0522* (2013.01); *A61B 5/4848* (2013.01); *A61B 2018/00404* (2013.01); *A61B 2018/00434* (2013.01); *A61B 2018/00511* (2013.01); *A61B 2018/00577* (2013.01); *A61B 2018/1861* (2013.01)

(58) Field of Classification Search
CPC ... A61B 5/0538; A61B 5/1076; A61B 5/6857; A61B 5/0522; A61B 5/4848; A61B 18/1492; A61B 18/1815; A61B 18/24; A61B 2018/00404; A61B 2018/00434; A61B 2018/00511; A61B 2018/00577; A61B 2018/1861
USPC .......................................................... 607/44
See application file for complete search history.

(56) References Cited

U.S. PATENT DOCUMENTS

| | | | |
|---|---|---|---|
| 4,764,504 A | 8/1988 | Johnson et al. | |
| 4,976,711 A | 12/1990 | Parins et al. | |
| 5,300,068 A | 4/1994 | Rosar et al. | |
| 5,358,514 A | 10/1994 | Schulman et al. | |
| 5,423,744 A | 6/1995 | Gencheff et al. | |
| 5,571,147 A | 11/1996 | Sluijter et al. | |
| 5,626,576 A | 5/1997 | Janssen | |
| 5,700,282 A | 12/1997 | Zabara | |
| 5,707,400 A | 1/1998 | Terry, Jr. et al. | |
| 5,865,787 A | 2/1999 | Shapland | |
| 5,944,710 A | 8/1999 | Dev et al. | |
| 5,983,141 A | 11/1999 | Sluijter et al. | |
| 6,004,269 A | 12/1999 | Crowley et al. | |
| 6,009,877 A | 1/2000 | Edwards | |
| 6,066,134 A | 5/2000 | Eggers et al. | |
| 6,099,524 A | 8/2000 | Lipson et al. | |
| 6,117,101 A | 9/2000 | Diederich et al. | |
| 6,149,620 A | 11/2000 | Baker et al. | |
| 6,161,048 A | 12/2000 | Sluijter et al. | |
| 6,219,577 B1 | 4/2001 | Brown, III et al. | |
| 6,224,592 B1 | 5/2001 | Eggers et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,405,732 B1 | 6/2002 | Edwards et al. | |
| 6,506,189 B1 | 1/2003 | Rittman et al. | |
| 6,514,226 B1 | 2/2003 | Levin et al. | |
| 6,522,926 B1 | 2/2003 | Kieval et al. | |
| 6,562,034 B2 | 5/2003 | Edwards et al. | |
| 6,635,054 B2 | 10/2003 | Fjield et al. | |
| 6,685,648 B2 | 2/2004 | Flaherty et al. | |
| 6,736,835 B2 | 5/2004 | Pellegrino et al. | |
| 6,845,267 B2 | 1/2005 | Harrison et al. | |
| 6,850,801 B2 | 2/2005 | Kieval et al. | |
| 6,885,888 B2 | 4/2005 | Rezai | |
| 6,893,436 B2 | 5/2005 | Woodard et al. | |
| 7,149,574 B2 | 12/2006 | Yun et al. | |
| 7,162,303 B2 | 1/2007 | Levin et al. | |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,617,005 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,778,703 B2 | 8/2010 | Gross et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,520 B2 | 4/2012 | Demarais et al. | |
| 8,175,711 B2 | 5/2012 | Demarais et al. | |
| 8,347,891 B2 | 1/2013 | Demarais et al. | |
| 8,777,942 B2 | 7/2014 | Wu et al. | |
| 8,888,773 B2 | 11/2014 | Chang et al. | |
| 8,998,894 B2 | 4/2015 | Mauch et al. | |
| 9,060,755 B2 | 6/2015 | Buckley et al. | |
| 9,084,610 B2 | 7/2015 | Goshgarian et al. | |
| 9,168,094 B2 | 10/2015 | Lee et al. | |
| 2003/0060858 A1 | 3/2003 | Kieval et al. | |
| 2005/0228460 A1 | 10/2005 | Levin et al. | |
| 2006/0004301 A1 | 1/2006 | Kasevich | |
| 2006/0206150 A1 | 9/2006 | Demarais et al. | |
| 2006/0271111 A1 | 11/2006 | Demarais et al. | |
| 2007/0129720 A1 | 6/2007 | Demarais et al. | |
| 2007/0265687 A1 | 11/2007 | Deem et al. | |
| 2008/0319513 A1 | 12/2008 | Pu et al. | |
| 2009/0036948 A1 | 2/2009 | Levin et al. | |
| 2010/0137860 A1 | 6/2010 | Demarais et al. | |
| 2010/0137952 A1 | 6/2010 | Demarais et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2012/0116382 A1 | 5/2012 | Ku et al. | |
| 2012/0130289 A1 | 5/2012 | Demarais et al. | |
| 2012/0130345 A1 | 5/2012 | Levin et al. | |
| 2012/0172837 A1 | 6/2012 | Demarais et al. | |
| 2013/0041269 A1* | 2/2013 | Stahmann ............ A61B 5/0295 600/484 |
| 2014/0012133 A1 | 1/2014 | Sverdik et al. | |
| 2015/0087927 A1* | 3/2015 | Manzke ................ A61B 5/065 600/301 |
| 2017/0215794 A1* | 8/2017 | Trudel ................. A61B 5/4833 |
| 2017/0348049 A1* | 12/2017 | Vrba ................. A61B 18/1492 |

FOREIGN PATENT DOCUMENTS

| | | |
|---|---|---|
| WO | WO2003057061 | 7/2003 |
| WO | WO2012061153 | 5/2012 |
| WO | WO2012061159 | 5/2012 |
| WO | WO2012061161 | 5/2012 |
| WO | WO2014159276 | 10/2014 |
| WO | WO2015113027 | 7/2015 |
| WO | WO2015143372 | 9/2015 |
| WO | WO2016054379 | 4/2016 |
| WO | WO2017012907 | 1/2017 |
| WO | WO2017136362 | 8/2017 |

OTHER PUBLICATIONS

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

(56) References Cited

OTHER PUBLICATIONS

Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Weber et al., "Changes in renal artery dimensions are associated with clinical response to radiofrequency renal denervation: a series of studies using quantitative angiography and intravascular ultrasound." Journal of Hypertension, Oct. 2017, vol. 35(10), pp. 2069-2076.
Brown, "Electrical impedance tomography (EIT): a review," Journal of Medical Engineering and Technology, vol. 27, No. 3, May/Jun. 2003, pp. 107-108.
Esler et al., "Renal Denervation: Not as Easy as it Looks," Science Translational Medicine, vol. 7, No. 285, Apr. 29, 2015, 4 pages.
Mahfoud et al., "Efficacy and Safety of Catheter-Based Radiofrequency Renal Denervation in Stented Renal Arteries," Circ Cardiovasc Interv. 2014; 7 :813-818.
Wolf et al., "Noninvasive assessment of lung volume: Respiratory inductance plethysmography and electrical impedance tomography." Crit Care Med 2005; vol. 33(3) Supplement.S163-S169.
Coulombe et al., "A Parametric Model of the Relationship Between EIT and Total Lung Volume." Physiol Meas 2005;26(4):401-411.
Zhang et al., "EIT Images of Ventilation: What Contributes to the Resistivity Changes?" Physiol. Meas., 2005, 26(2): S81-S92.
Brown, "Electrical impedance tomography (EIT): a review," Journal of Medical Engineering & Technology. 2003; 27:97-108.
U.S. Appl. No. 62/588,215, by Hettrick et al, filed Nov. 17, 2017.
U.S. Appl. No. 15/965,687, by Coates et al., filed Apr. 27, 2018.
U.S. Appl. No. 15/965,692, by Coates et al., filed Apr. 27, 2018.
U.S. Appl. No. 15/965,675, by Coates et al., filed Apr. 27, 2018.

\* cited by examiner

SYSTEMS AND METHODS FOR ASSESSING THE EFFICACY OF NEUROMODULATION THERAPY

CROSS-REFERENCE TO RELATED APPLICATION(S)

The present application claims the benefit of U.S. Provisional Patent Application No. 62/621,285, filed Jan. 24, 2018, the disclosure of which is incorporated herein by reference in its entirety.

TECHNICAL FIELD

The present technology is related to neuromodulation. In particular, various embodiments of the present technology are related to systems and methods for periprocedurally assessing the efficacy of neuromodulation therapy.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

DETAILED DESCRIPTION

Figure 1A:
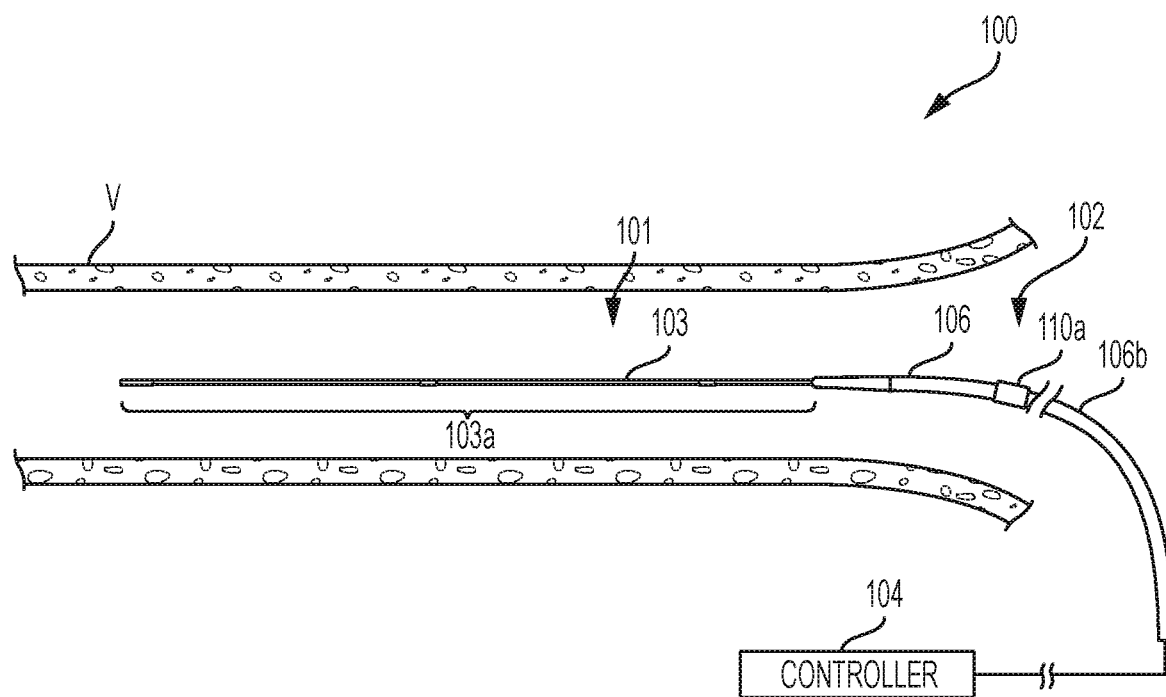
FIG. 1A is a partially schematic side view of a neuromodulation system with a distal portion of a guidewire positioned within a blood vessel of a human patient in accordance with embodiments of the present technology.

Systems and methods in accordance with embodiments of the present technology can be configured to obtain measurements related to a dimension of a renal blood vessel before, during, and/or after a neuromodulation procedure (e.g., a renal denervation procedure) to periprocedurally assess the efficacy of the neuromodulation procedure (e.g., to assess a particular patient's likelihood of deriving a therapeutic benefit from delivered neuromodulation energy). In particular, recent research suggests that there is a strong correlation between the reduction in renal blood vessel diameter following a renal denervation procedure and the ultimate efficacy of the procedure (e.g., an ultimate drop in blood pressure). Therefore, measuring the reduction in renal blood vessel diameter—or a related value—after a neuromodulation procedure is expected to provide periprocedural information about the success (or lack thereof) of the neuromodulation procedure.

Currently, there are only limited means available for a practitioner performing a neuromodulation procedure to know immediately after performing the procedure whether the procedure was successful. Indeed, because of the complexity of the sympathetic nervous system response to neuromodulation, the practitioner must often wait weeks or months to determine the success of a neuromodulation procedure. Moreover, current techniques for measuring the post-procedure diameter of renal blood vessels include quantitative angiography and intravascular ultrasound. These techniques require additional devices and procedures, and can be slow, expensive, and relatively inaccurate.

In contrast with conventional techniques, in several of the embodiments described below, a neuromodulation system can include a neuromodulation catheter configured to both (i) deliver therapeutic neuromodulation at a target site in a renal blood vessel and (ii) detect one or more measurements related to a dimension of the renal blood vessel. A controller can receive the one or more measurements, compare the measurements to a baseline measurement (e.g., a pre-procedure measurement), and assess the efficacy of delivered neuromodulation energy based, at least in part, on the comparison. Accordingly, systems configured in accordance with the present technology are expected to provide a near real-time periprocedural assessment of the efficacy of a neuromodulation procedure by detecting a simple post-neuromodulation measurement of the renal blood vessel in which the neuromodulation is carried out—without the need for expensive and untimely additional measurements using separate, conventional, measurement systems.

Specific details of several embodiments of the present technology are described herein with reference to FIGS. 1A-10. Although many of the embodiments are described with respect to devices, systems, and methods for intravascular renal neuromodulation, other applications and other embodiments in addition to those described herein are within the scope of the present technology. For example, at least some embodiments of the present technology may be useful for intraluminal neuromodulation, extravascular neuromodulation, non-renal neuromodulation, and/or use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

I. Selected Embodiments of Neuromodulation Catheters and Systems

Figure 1B:
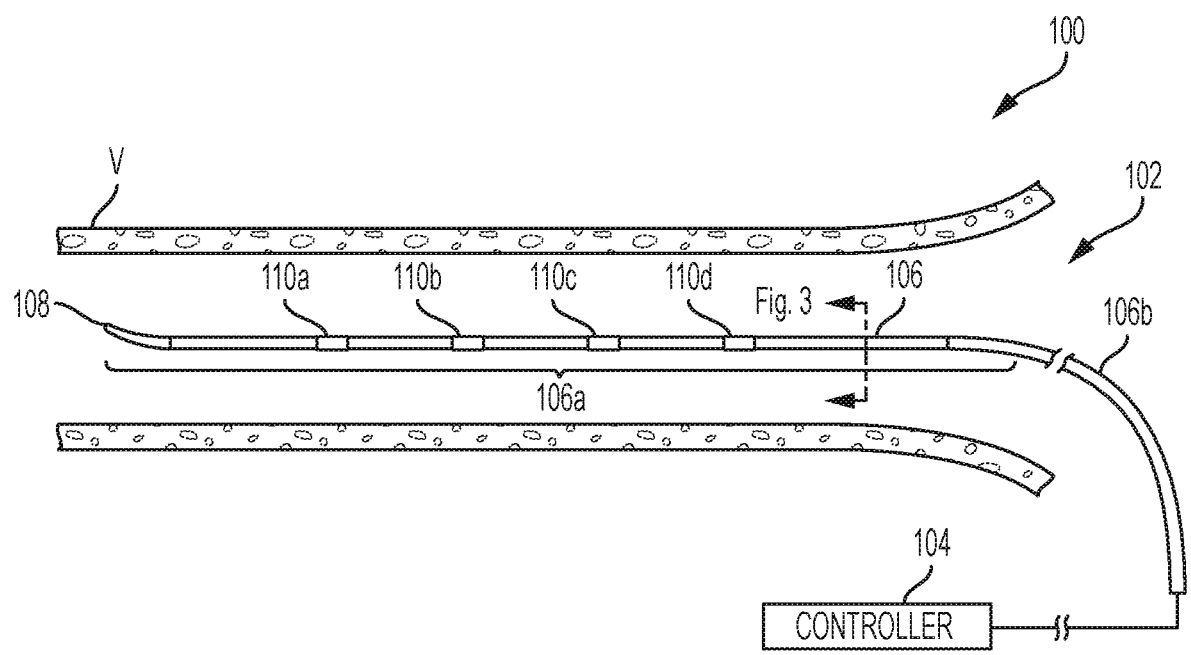
FIGS. 1B and 1C are partially schematic side views of the neuromodulation system shown in FIG. 1A with a distal portion of a neuromodulation catheter in a first state and a second state, respectively, within the blood vessel of the human patient in accordance with embodiments of the present technology.
Figure 1C:
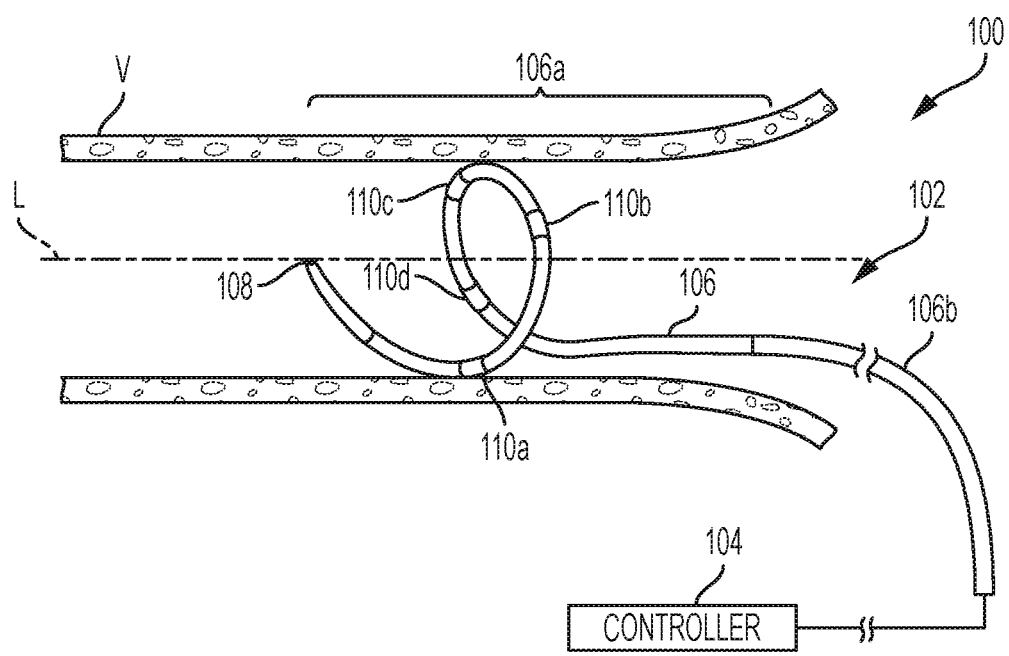

FIGS. 1A-1C are partially schematic side views of a neuromodulation system 100 ("system 100") configured in accordance with an embodiment of the present technology and shown in different arrangements while positioned at a target site within a blood vessel V (e.g., a renal artery) of a human patient. The system 100 includes a guidewire 101 (only visible in FIG. 1A) and a neuromodulation catheter 102 that can be advanced over the guidewire 101 to the target site within the blood vessel V. In other embodiments, the neuromodulation catheter 102 can be configured for delivery to the target site via other methods (e.g., via a guide catheter, via sheath retraction, via a pull-wire, etc.). The neuromodulation catheter 102 is configured to perform neuromodulation therapy at the target site to, for example, ablate nerves proximate the wall of the blood vessel V. As discussed in greater detail below, the neuromodulation catheter 102 is further configured to detect one or more measurements related to a dimension (e.g., a diameter, a cross-sectional area, a circumference, a segmental volume, etc.) of the blood vessel V before, during, and/or after neuromodulation therapy to assess the efficacy of a given neuromodulation therapy or procedure. The system 100 further includes one or more controllers 104 communicatively coupled to the neuromodulation catheter 102 via a wired or wireless communication link.

Figure 3:
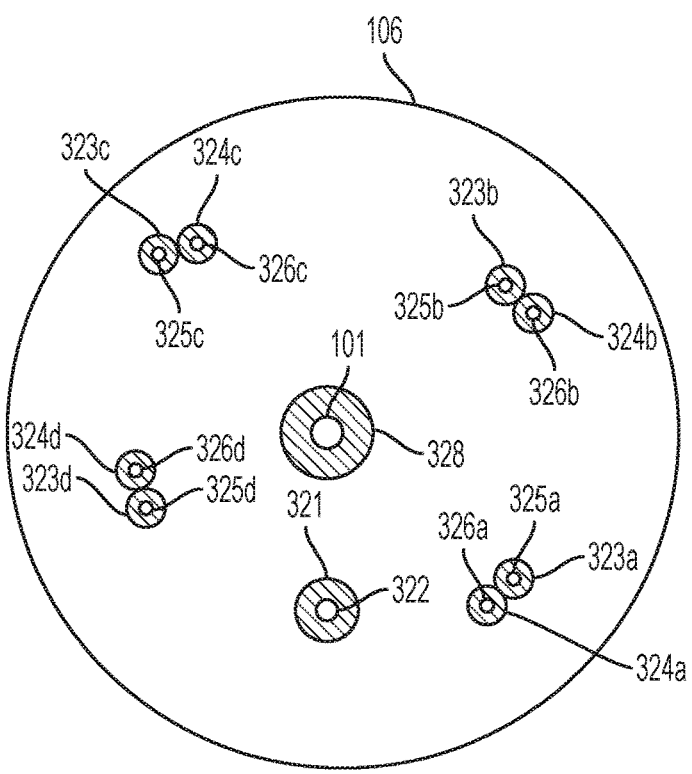
FIG. 3 is a cross-sectional view of the neuromodulation catheter shown in FIG. 1C with an optical element configured in accordance with embodiments of the present technology.

Referring to FIG. 1A, the guidewire 101 includes an elongated member 103 having a distal portion 103a configured to be positioned at the target site within the blood vessel V and a proximal portion (not visible) that extends outside of the patient to a handle (not shown) or other feature(s) that allow an operator to manipulate the distal portion 103a to the desired position/orientation. The elongated member 103 can be sized to be slidably positioned within a lumen of the neuromodulation catheter 102 (e.g., as shown in FIG. 3). One or more portions of the elongated member 103 can comprise, for example, a solid wire and/or a wire coil. For example, in some embodiments, the proximal portion of the elongated member 103 comprises a solid wire and the distal portion 103a comprises a wire coil. In other embodiments, however, the elongated member 103 comprises only a solid wire or only a wire coil. In still other embodiments, the elongated member 103 comprises other suitable components and/or configurations. Additionally, the elongated member 103 can have a uniform stiffness along its length, or can have a stiffness that varies along its length.

As best shown in FIG. 1B, the neuromodulation catheter 102 includes an elongated shaft 106 configured to be slidably delivered over the guidewire 101. The elongated shaft 106 has a distal portion 106a configured to be intravascularly positioned at the target site within the blood vessel V and a proximal portion 106b extending outside of the patient to a handle (not shown) or other feature(s) that allow an operator to manipulate the distal portion 106a of the elongated shaft 106. As shown in FIGS. 1B and 1C, for example, the neuromodulation catheter 102 is transformable between a first state or arrangement in which the distal portion 106a of the elongated shaft 106 is at least generally straight (FIG. 1B), and a second (e.g., deployed, expanded, etc.) state or arrangement in which the distal portion 106a is transformed or otherwise expanded to a spiral/helical shape (FIG. 1C).

Referring to FIGS. 1B and 1C together, the neuromodulation catheter 102 includes a plurality of energy delivery elements, such as electrodes 110 spaced along the distal portion 106a of the elongated shaft 106, and a distal tip 108 (e.g., an atraumatic tip). In the illustrated embodiment, the neuromodulation catheter 102 includes four electrodes 110 (identified individually as first through fourth electrodes 110a-110d, respectively). In other embodiments, however, the neuromodulation catheter 102 may include one, two, three, or more than four electrodes 110, and/or may include different energy delivery elements. The electrodes 110 are configured to deliver neuromodulation energy to the target site to modulate or ablate nerves (e.g., renal nerves) proximate to the target site. In other embodiments, the neuromodulation catheter 102 can include electrodes, transducers, or other elements to delivery energy to modulate nerves using other suitable neuromodulation modalities, such as pulsed electrical energy, microwave energy, optical energy, ultrasound energy (e.g., intravascularly delivered ultrasound and/or high-intensity focused ultrasound (HIFU)), direct heat energy, radiation (e.g., infrared, visible, and/or gamma radiation), and/or other suitable types of energy. In certain embodiments, the neuromodulation catheter 102 may be configured for cryotherapeutic treatment, and can apply cryogenic cooling to the vessel V with a refrigerant (e.g., via a balloon catheter that circulates the refrigerant).

The dimensions (e.g., outer diameter and length) of the distal portion 106a of the elongated shaft 106 (e.g., the portion that takes on the spiral/helical shape in the second state illustrated in FIG. 1C) can be selected to accommodate the vessels or other body lumens in which the distal portion 106a is designed to be delivered. For example, when in the second state, the axial length of the distal portion 106a of the elongated shaft 106 may be selected to be no longer than a patient's renal artery (e.g., typically less than 7 cm), and have a diameter that accommodates the inner diameter of a typical renal artery (e.g., about 2-10 mm). In other embodiments, the distal portion 106a of the elongated shaft 106 can have other dimensions depending on the body lumen within which it is configured to be deployed. In further embodiments, the distal portion 106a of the elongated shaft 106 can have other suitable shapes (e.g., semi-circular, curved, straight, etc.), and/or the neuromodulation catheter 102 can include multiple support members configured to carry one or more electrodes 110. The distal portion 106a of the elongated shaft 106 may also be designed to apply a desired outward radial force to a vessel when expanded to the spiral/helical second state to place one or more of the electrodes 110 in contact with the vessel wall.

In some embodiments, the system 100 includes a console (not shown), and the controller 104 is integrated with the console. In such embodiments, the console can be configured to communicate with the neuromodulation catheter 102 via a wireless and/or wired communication link. For example, in some embodiments the console can include an access port for receiving a wired connection to the neuromodulation catheter 102.

Although the embodiment of the neuromodulation catheter 102 shown in FIGS. 1A-1C has a spiral/helically-shaped configuration, in other embodiments, the neuromodulation catheter 102 can have other suitable shapes, sizes, and/or configurations. Other suitable devices and technologies are described in, for example, U.S. Pat. Nos. 8,777,942; 9,084,610; 9,060,755; 8,998,894; PCT Application No. PCT/US2011/057754, filed Oct. 25, 2011; and U.S. Pat. No. 8,888,773. All of the foregoing applications are incorporated herein by reference in their entireties. Non-limiting examples of devices and systems include the the Symplicity Spyral™ multielectrode RF ablation catheter and the Arctic Front Advance™ cardiac cryoablation system.

II. Selected Embodiments of Sensing Elements for Assessing the Efficacy of Neuromodulation Therapy As described above, it is expected that a successful or effective neuromodulation therapy (e.g., when nerves are ablated to a desired degree) causes a reduction in the diameter of the ablated blood vessel. Accordingly, it may be advantageous to detect one or more measurements related to a dimension of a blood vessel of a patient in order to determine a reduction—or lack thereof—in the dimension of the blood vessel as a result of neuromodulation therapy and, correlatively, an efficacy of the neuromodulation therapy. In general, as detailed below, the system 100 of the present technology includes at least one sensing element configured to detect one or more measurements related to a dimension of a blood vessel before, during, and/or after delivery of neuromodulation energy to that blood vessel.

For example, in some embodiments, the sensing element can comprise one or more of the electrodes 110 at the distal portion 106a of the elongated shaft 106 of the neuromodulation catheter 102 ("the distal portion of the neuromodulation catheter 102"). The electrodes 110 can be configured to (i) generate one more signals (e.g., electrical signals) at and/or proximate to the target site in the blood vessel V before and/or after neuromodulation, and (ii) detect the signals after the signals have propagated through at least a portion of the blood vessel V. Accordingly, the measurements related to the dimension of the blood vessel V can include, for example, propagation times of the signals between one or more of the electrodes 110. In some embodiments, the controller 104 is operably coupled to the electrodes 110 and configured to (i) deliver neuromodulation energy to the target site within the blood vessel V via the electrodes 110, (ii) generate and detect one or more signals for measuring the dimension of the blood vessel via the electrodes 110, and (iii) determine a propagation time, attenuation degree, or other measurement (e.g., property) of the detected one or more signals.

Figure 2:
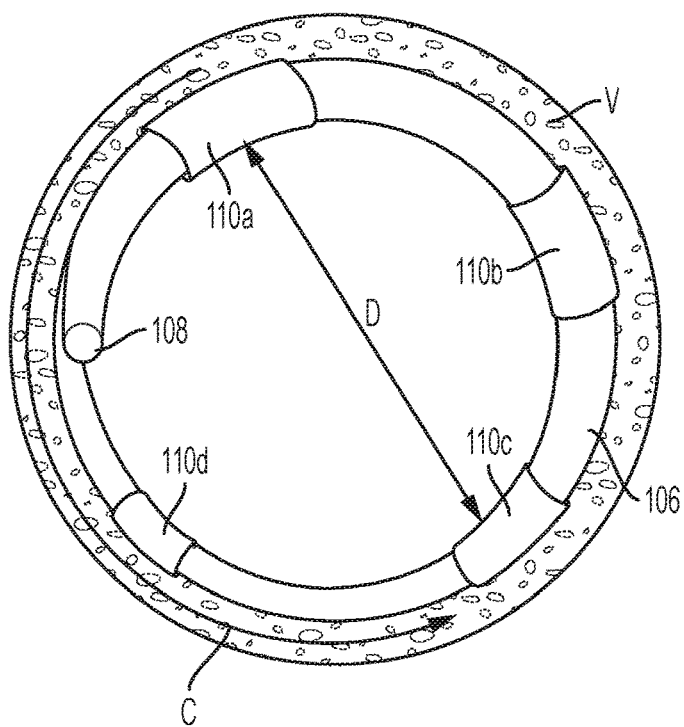
FIG. 2 is a front view of the neuromodulation catheter shown in FIG. 1C looking proximally down a longitudinal axis of the blood vessel of the human patient.

More particularly, FIG. 2 is a front view of the distal portion of the neuromodulation catheter 102 in the second state shown in FIG. 1C, and looking down a longitudinal axis L (shown in FIG. 1C) of the blood vessel V in the proximal direction. As shown in FIG. 2, a signal generated at one of the electrodes 110 can propagate between the electrodes 110 through a path in the wall of the blood vessel V, as indicated by arrow C, or through the blood or other medium in the lumen of the blood vessel V, as indicated by arrow D. Moreover, the same signal can be detected at multiple ones of the electrodes 110 and/or at the same electrode 110 that generates the signal. In some embodiments, the system 100 is configured to detect the propagation time of a signal from electrodes 110 that are spaced about 180 degrees apart relative to an inner surface of the blood vessel V. For example, in certain embodiments, a signal can be generated/detected at the first electrode 110a and detected/generated at the third electrode 110c.

Regardless of the combination of electrodes 110 that are used to generate and detect signals that propagate through the blood vessel V, the propagation time, attenuation degree, and/or other measurement of the signals can be generally indicative of a physical dimension of the blood vessel V. That is, for example, a longer propagation time between generation and detection of a signal can indicate that the blood vessel V has a larger diameter while a shorter propagation time can indicate that the blood vessel V has a smaller diameter. Similarly, in some embodiments, the degree of attenuation of a waveform of a detected signal can be correlated to the distance the signal traveled through the (e.g., less conductive) blood vessel V. In some embodiments, the difference in arrival time of the same signal as a result of different conduction paths can provide additional information for determining a dimension of the blood vessel V. For example, the (e.g., longer) conduction path of a signal through the wall of the blood vessel V (arrow C) may be detectable a measurable time after the (e.g., shorter) conduction path of the same signal through the blood or other medium in the lumen of the blood vessel V (arrow D.) As discussed in further detail below, in some embodiments, measurements detected by the electrodes 110 can be used to determine an actual (e.g., absolute) dimension of the blood vessel V while, in other embodiments, measurements can be compared to a baseline measurement to determine a percentage change (e.g., reduction) in the dimension of the blood vessel V.

In some embodiments, the signals generated at the electrodes 110 can have a specific, known, waveform shape that distinguishes the signals from other signals that may be naturally occurring and detectable in the blood vessel V. For example, in certain embodiments, the controller 104 can generate signals having a delta, saw tooth, or another distinguishable waveform shape. Thus, while detected signals may be attenuated, they can retain the same waveform shape such that they are easily distinguishable by the controller 104. In some embodiments, the degree of attenuation of the detected signals can be used to determine the path of the signal through the blood vessel V—for example, through the lumen of the blood vessel V (e.g., along the path indicated by the arrow D) or through the wall of the blood vessel V (e.g., along the path indicated by the arrow C.)

In certain embodiments, the sensing element of the system 100 can comprise a separate component positioned at the distal portion of the neuromodulation catheter 102. For example, FIG. 3 is a cross-sectional view of the distal portion of the neuromodulation catheter 102 taken along the reference line indicated in FIG. 1B and in accordance with another embodiment of the present technology. As illustrated in the embodiment of FIG. 3, the sensing element can comprise an optical element 322 positioned within an optical element lumen 321 extending at least within the distal portion of the neuromodulation catheter 102 and configured to detect measurements related to a dimension of the blood vessel V.

As shown in FIG. 3, the distal portion of the neuromodulation catheter 102 further includes: (i) transmission lumens 323 (identified individually as first through fourth transmission lumens 323a-323d, respectively) each containing a transmission wire 325 therein (identified individually as first through fourth transmission wires 325a-325d, respectively), (ii) reception lumens 324 (identified individually as first through fourth reception lumens 324a-324d, respectively) each containing a reception wire 326 therein (identified individually as first through fourth reception wires 326a-326d, respectively), and (iii) a guidewire lumen 328 carrying the guidewire 101 therein. The transmission and reception wires 325, 326 operatively couple corresponding one of the electrodes 110 to, for example, the controller 104 such that the controller 104 can send and receive signals (e.g., measurement signals as described above with reference to FIG. 2) and/or neuromodulation energy to and from the electrodes 110 via the transmission and reception wires 325, 326. In other embodiments, the electrodes 110 are wirelessly coupled to the controller 104 and/or other components of the system 100.

In the embodiment illustrated in FIG. 3, the guidewire lumen 328 is axially aligned with a central axis of the neuromodulation catheter 102 while the optical element lumen 321 is positioned off the central axis of the neuromodulation catheter 102. In some such embodiments, it is advantageous to concentrically position the guidewire 101 within the neuromodulation catheter 102 to facilitate advancement and positioning of the neuromodulation catheter 102 within the blood vessel V. However, in other embodiments, the optical element lumen 321 may be axially aligned with the central axis of the neuromodulation catheter 102. Moreover, in certain embodiments, the guidewire 101 and the optical element 322 can be combined into a single, integral, component (e.g., the guidewire 101 can at least partially comprise an optical fiber).

In some embodiments, the optical element 322 can comprise an optical fiber having a fiber Bragg grating positioned at or proximate to the distal portion of the neuromodulation catheter 102. The fiber Bragg grating can be configured to reflect particular wavelengths of light and transmit all others. The transmission/reflection pattern (e.g., the particular transmitted/reflected wavelengths) of the fiber Bragg grating can be a function of, for example, the strain on the fiber Bragg grating and/or an amount of bend in the fiber Bragg grating. Thus, the transmission/reflection pattern of the optical element 322 can vary as the distal portion of the neuromodulation catheter 102 changes diameter in conformance with the diameter of the blood vessel V. Accordingly, in certain embodiments, the optical fiber of the optical element 322 extends to and/or is operatively coupled to the controller 104, and the controller 104 is configured to (i) transmit optical signals distally along the optical fiber to the fiber Bragg grating of the optical element 322, and (ii) measure the reflection pattern that is transmitted proximally along the optical fiber as a result of the fiber Bragg grating.

Each of the embodiments described above with reference to FIGS. 2 and 3 share the advantage that a measurement related to a dimension of the blood vessel V can be detected using the neuromodulation catheter 102. The measurement can be used to assess the efficacy of neuromodulation therapy delivered via the neuromodulation catheter 102 without the need for additional devices or procedures (e.g., quantitative angiography, intravascular ultrasound, etc.). Thus, embodiments of the present technology are expected to more quickly and cheaply determine the efficacy of neuromodulation therapy, since the same device may be used to both deliver neuromodulation energy to a vessel and detect a reduction in a dimension of that same vessel. As described in further detail below, the present technology may also permit a practitioner to use the determined efficacy as a guide for whether additional neuromodulation is necessary or desirable.

Moreover, one advantage of the embodiment described above with reference to FIG. 2 is that no physical modifications need to be made to the neuromodulation catheter 102. That is, the same electrodes 110 that deliver neuromodulation energy may be used to determine a dimension of the blood vessel V. In some embodiments, however, this may inhibit the simultaneous detection of measurements related to a dimension of the blood vessel V and delivery of neuromodulation energy. While the embodiment described with reference to FIG. 3 requires an additional component—the optical element 322—it may enable such simultaneous vessel measurement and delivery of neuromodulation energy since the optical element 322 is a separate component.

In other embodiments, the sensing element of the system 100 can comprise other components suitable for detecting a measurement related to a dimension of the blood vessel V. For example, in some embodiments, induction coils can be positioned at the distal portion of the neuromodulation catheter 102 (e.g., proximate the electrodes 110). A current can be driven through at least a first one of the induction coils to generate a magnetic field that induces a current in and is thus is detectable at the other induction coils. The measured induced current can correlate to the distance separating the induction coils. In certain embodiments, a current can be driven through a first induction coil to induce a current in a second induction coil that is about 180 degrees apart from the first induction coil relative to an inner surface of the blood vessel V. Thus, the determined distance between the first and second induction coils can approximate the diameter of the blood vessel V.

III. Selected Methods for Assessing the Efficacy of Neuromodulation Therapy

Figure 4:
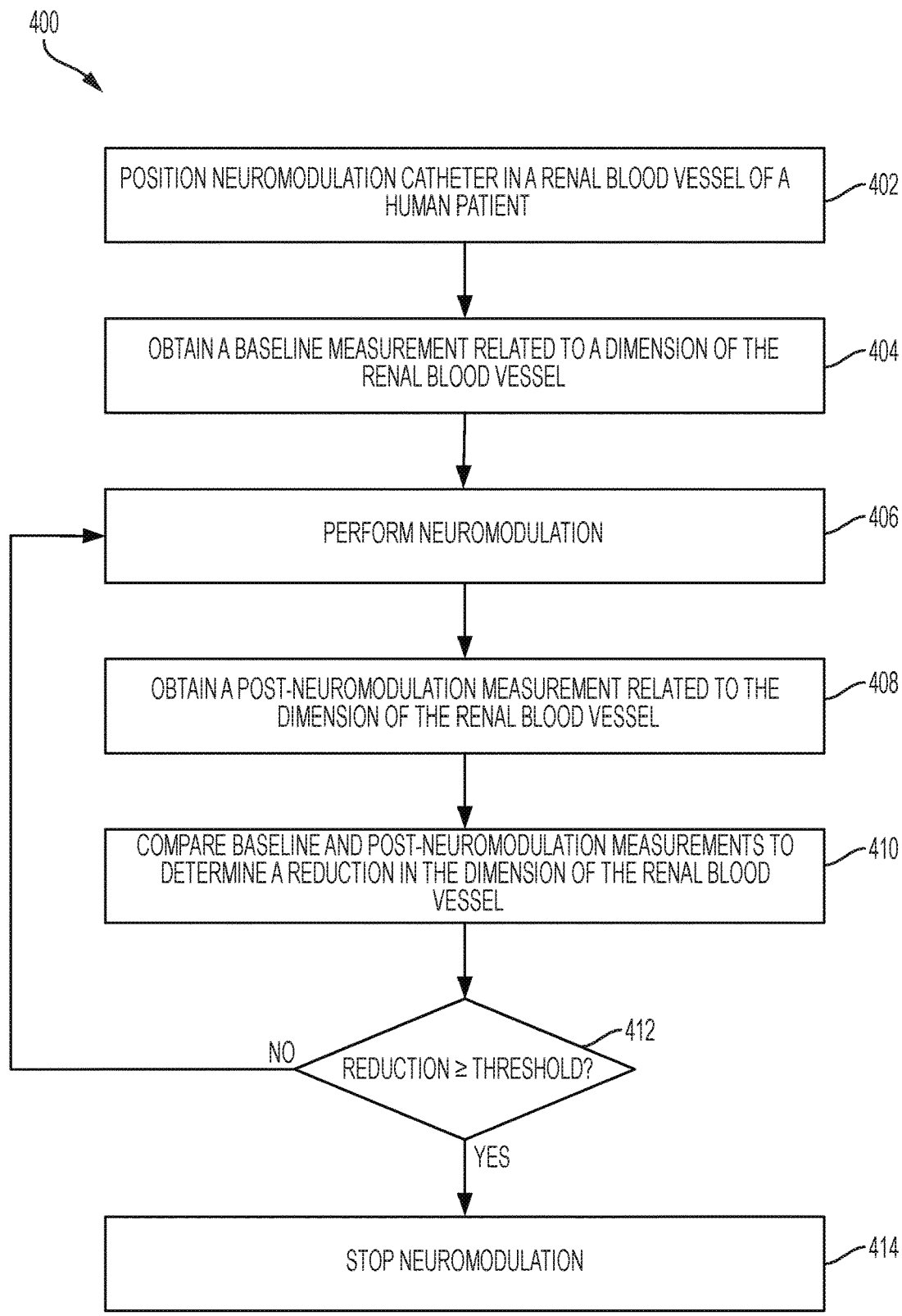
FIG. 4 is a flow diagram of a process or method for assessing the efficacy of neuromodulation therapy in accordance with embodiments of the present technology.

FIG. 4 is a flow diagram of a method or process 400 for evaluating the efficacy of neuromodulation therapy in accordance with embodiments of the present technology. The method 400 can be implemented using the system 100 described above with reference to FIGS. 1A-3 and/or using other suitable systems for evaluating the efficacy of neuromodulation therapy. For example, the neuromodulation catheter 102 and/or the controller 104 can be used to perform the various steps of the method 400. Accordingly, for sake of illustration, some features of the method 400 will be described in the context of the embodiments shown in FIGS. 1A-3.

Beginning at block 402, the method includes positioning the neuromodulation catheter 102 at a target site within the blood vessel V of the human patient. In some embodiments, positioning the neuromodulation catheter 102 includes (i) positioning the guidewire 101 along a portion of the blood vessel V proximate the target site (FIG. 1A), (ii) advancing the neuromodulation catheter 102 over the guidewire 101 to the target site (FIG. 1B), and (iii) transforming or otherwise expanding the distal portion of the neuromodulation catheter 102 to the spiral/helical shape in which the electrodes 110 contact the wall of the blood vessel V (FIG. 1C).

At block 404, the method includes determining one or more baseline measurements related to a dimension of the blood vessel V. The baseline measurement can be a direct measure of a dimension of the blood vessel V (e.g., the diameter, circumference, etc.) or a measurement related to a dimension of the blood vessel V, as described above (e.g., a propagation time of an electric signal through the blood vessel V). In some embodiments, the sensing element of the neuromodulation catheter 102 can be used to determine the baseline measurement. For example, in certain embodiments, wherein the sensing element comprises the electrodes 110 (FIG. 2), the controller 104 can be configured to (i) control the electrodes 110 to generate and detect one or more signals that propagate through the blood vessel V and (ii) determine a baseline measurement (e.g., a propagation time) related to the dimension of the blood vessel V. In other embodiments, where the sensing element comprises the optical element 322 (FIG. 3), the controller 104 can be configured to (i) transmit an optical signal to the optical element 322, and (ii) receive an optical signal reflected from the distal portion of the neuromodulation catheter 102. In such an embodiment, the baseline measurement related to the dimension of the blood vessel V can be the reflected optical signal itself, or a corresponding property of the optical element 322 such as a diameter, amount of strain, etc.

In still other embodiments, the sensing element of the neuromodulation catheter 102 is not used to determine the baseline measurement and the baseline measurement is obtained via other methods (e.g., quantitative angiography, intravascular ultrasound, etc.) prior to positioning of the neuromodulation catheter 102 (block 402). Moreover, the baseline measurement can be a single measurement or a composite or average of several different measurements. For example, the baseline measurement can be an average of several measurements taken over a period of seconds (e.g., about 0.5 second, about 1 second, about 2 seconds, etc.) to account for changes in the dimensions of the blood vessel V during the cardiac cycle (e.g., to account for differing vessel diameters during systole and diastole). In some embodiments, the obtained baseline measurements can be communicated to and stored in the memory of the controller 104 and/or another component of the system 100.

At block 406, the method includes performing neuromodulation therapy with the neuromodulation catheter 102 at the target site in the blood vessel V to, for example, ablate nerves proximate to the wall of the blood vessel V. For example, the method 400 can include applying RF energy (e.g., via the electrodes 110), pulsed electrical energy, microwave energy, optical energy, ultrasound energy (e.g., intravascularly delivered ultrasound and/or HIFU), direct heat energy, radiation, cryogenic cooling, chemical-based treatment, and/or another suitable type of neuromodulation energy.

At block 408, the method includes determining one or more post-neuromodulation measurements related to the dimension of the blood vessel V. The sensing element of the neuromodulation catheter can be used to obtain the post-neuromodulation measurements in generally the same manner as the baseline measurements described above with reference to block 404. The one or more post-modulation measurements can include a single measurement or a composite or average of several different measurements. In some embodiments, the obtained post-modulation measurements are communicated to the controller 104 and stored in the memory of the controller 104 and/or another component of the system 100.

At block 410, the method includes comparing the obtained baseline measurements (block 404) and obtained post-neuromodulation measurements (block 408) to determine a reduction in a dimension of the blood vessel V, if any, as a result of the neuromodulation therapy (block 406). In some embodiments, the comparison can be performed automatically by the controller 104 and/or another component of the system 100. In certain embodiments, the determined reduction in the dimension of the blood vessel V is an absolute reduction measured in units of length, area, volume, etc. In other embodiments, the determined reduction is a percentage reduction in the dimension. For example, a baseline propagation time of a signal travelling between one or more of the electrodes 110 can be compared to a post-modulation propagation time of a signal travelling between the same electrode(s) 110 to determine the percentage reduction. In some embodiments, the determined reduction in the dimension of the blood vessel V can be used to assess the efficacy of the performed modulation therapy by, for example, correlating the percentage reduction to expected results (e.g., an expected drop in blood pressure at a certain point after a renal denervation procedure).

In certain embodiments, at block 412, the determined reduction in the dimension of the blood vessel V can be compared to a threshold value. The threshold value, for example, can be equivalent to a percentage reduction (e.g., 5% reduction, 10% reduction, 15% reduction, 20% reduction, 50% reduction, etc.) in the vessel dimension or a predefined absolute reduction in vessel dimension (e.g., a vessel diameter reduction value associated with effective neuromodulation, and/or a value based on other factors associated with successful neuromodulation).

If the difference is greater than or equal to the predetermined threshold, the operator can elect to stop neuromodulation therapy at block 414. In some embodiments, the operator can then remove the neuromodulation catheter 102 from the blood vessel V, or reposition the neuromodulation catheter 102 to a different target site for delivering additional neuromodulation energy to the different target site.

If the difference is less than the predetermined threshold, the operator can elect to apply one or more additional rounds of neuromodulation therapy to the treatment site using the same energy level or a higher energy level. After the additional neuromodulation therapy, the operator can subsequently detect the change, if any, in vessel dimension as described above. In such situations, the controller 104 and/or another component of the system 100 can be configured to store the post-neuromodulation measurement (block 408) as the new baseline measurement. In certain embodiments, the operator can alternatively or additionally reposition the distal portion of the neuromodulation catheter 102 along the blood vessel V to apply neuromodulation energy to a different target site and determine a reduction in the dimension of the blood vessel V at the different target site.

As described above, research suggests that there is a strong correlation between the reduction in renal blood vessel diameter following a renal denervation procedure and the ultimate efficacy of the procedure (e.g., an ultimate drop in blood pressure). Accordingly, comparing measurements related to the diameter of the blood vessel before and after neuromodulation is expected to provide one indication of whether a neuromodulation procedure is successful. Accordingly, the system 100 is expected to provide practitioners with a near real time indication of whether a successful neuromodulation treatment has occurred. Thus, practitioners do not need to wait until after the procedure—in some instances for months—to determine whether the treatment was effective. Moreover, any additional neuromodulation energy applications necessary to effectuate neuromodulation can be performed while the neuromodulation catheter 102 is still within the blood vessel V. Accordingly, the system 100 can facilitate efficient and effective neuromodulation treatments.

IV. Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic over activity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable treatment sites during a treatment procedure. The treatment site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a treatment site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., HIFU energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., HIFU energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

V. Related Anatomy and Physiology

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 5:
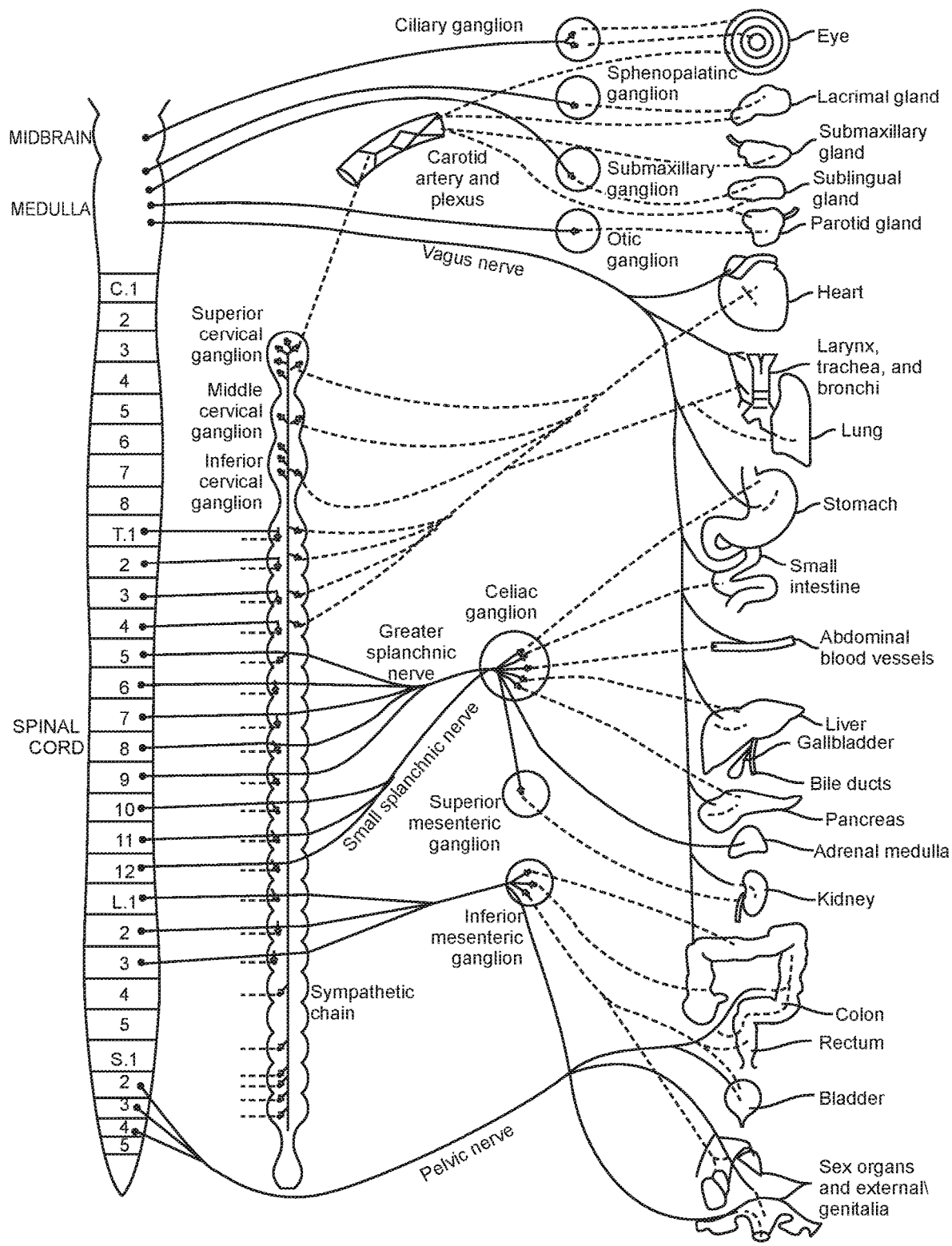
FIG. 5 is a conceptual illustration of the sympathetic nervous system (SNS) and how the brain communicates with the body via the SNS.

As shown in FIG. 5, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 6:
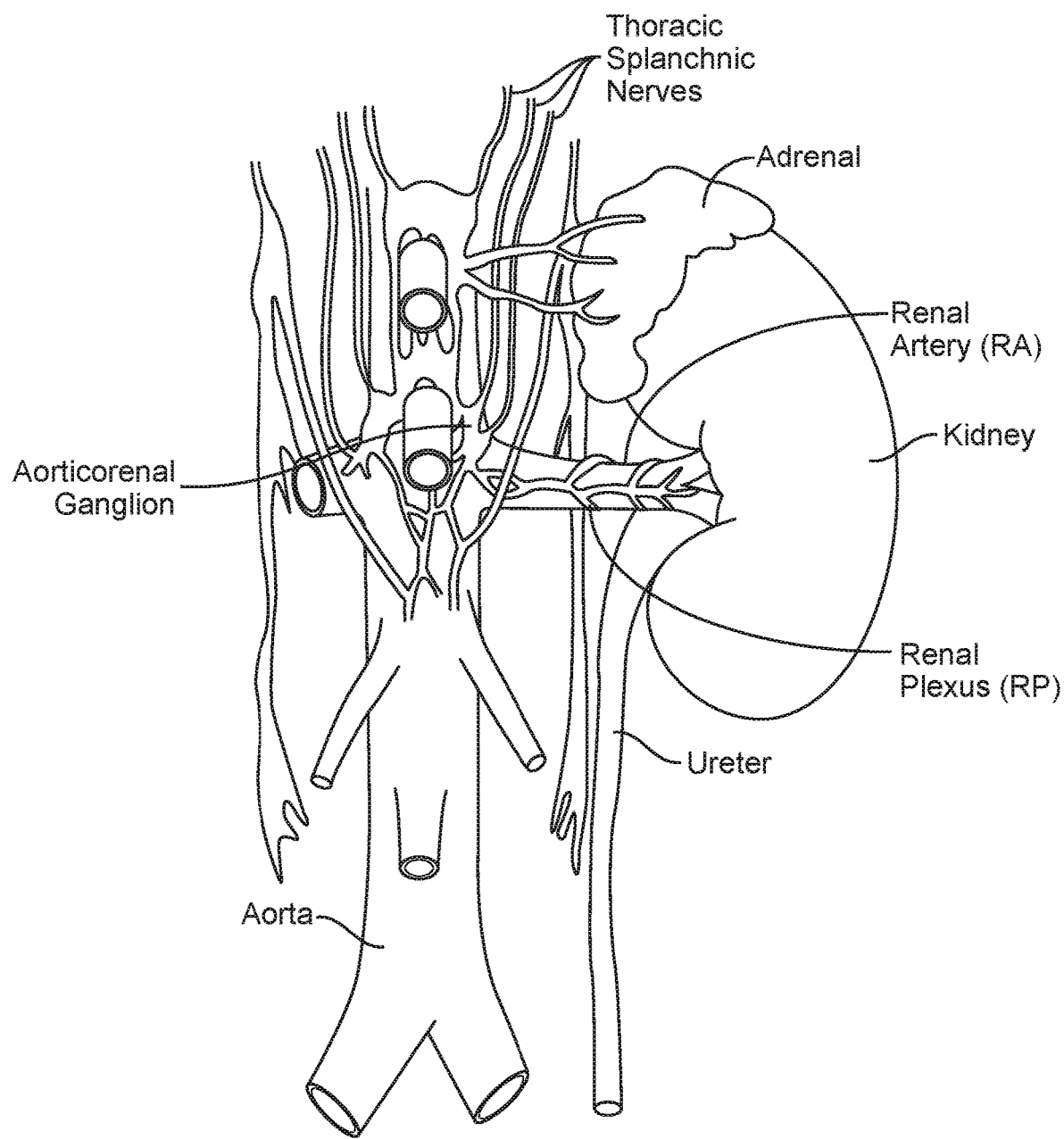
FIG. 6 is an enlarged anatomic view of nerves innervating a left kidney to form the renal plexus surrounding the left renal artery.

As FIG. 6 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 7:
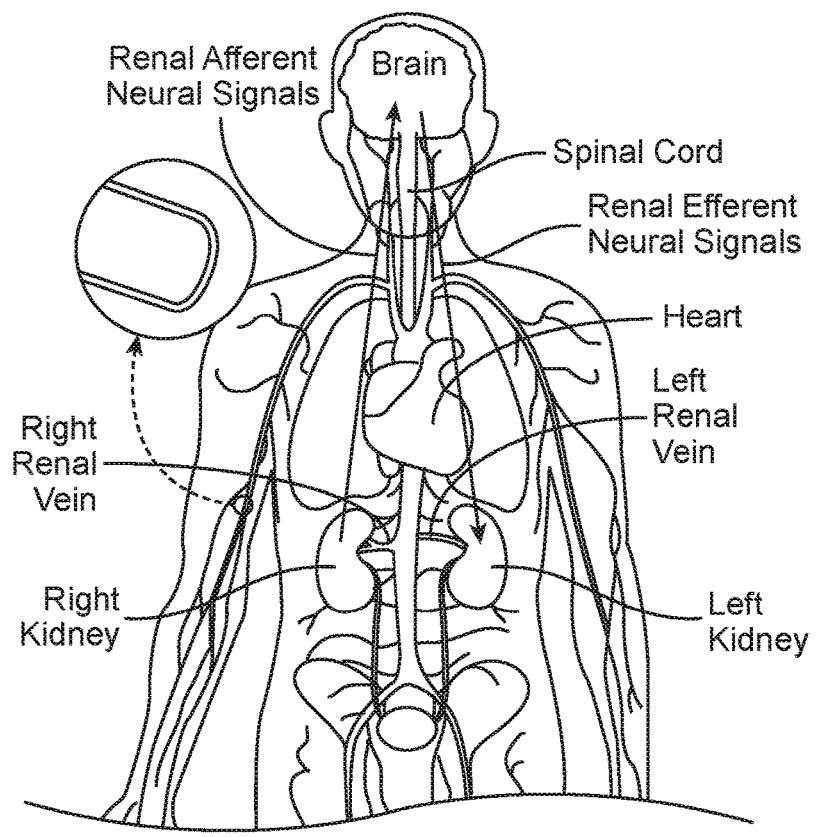
FIGS. 7 and 8 are anatomic and conceptual views, respectively, of a human body depicting neural efferent and afferent communication between the brain and kidneys.
Figure 8:
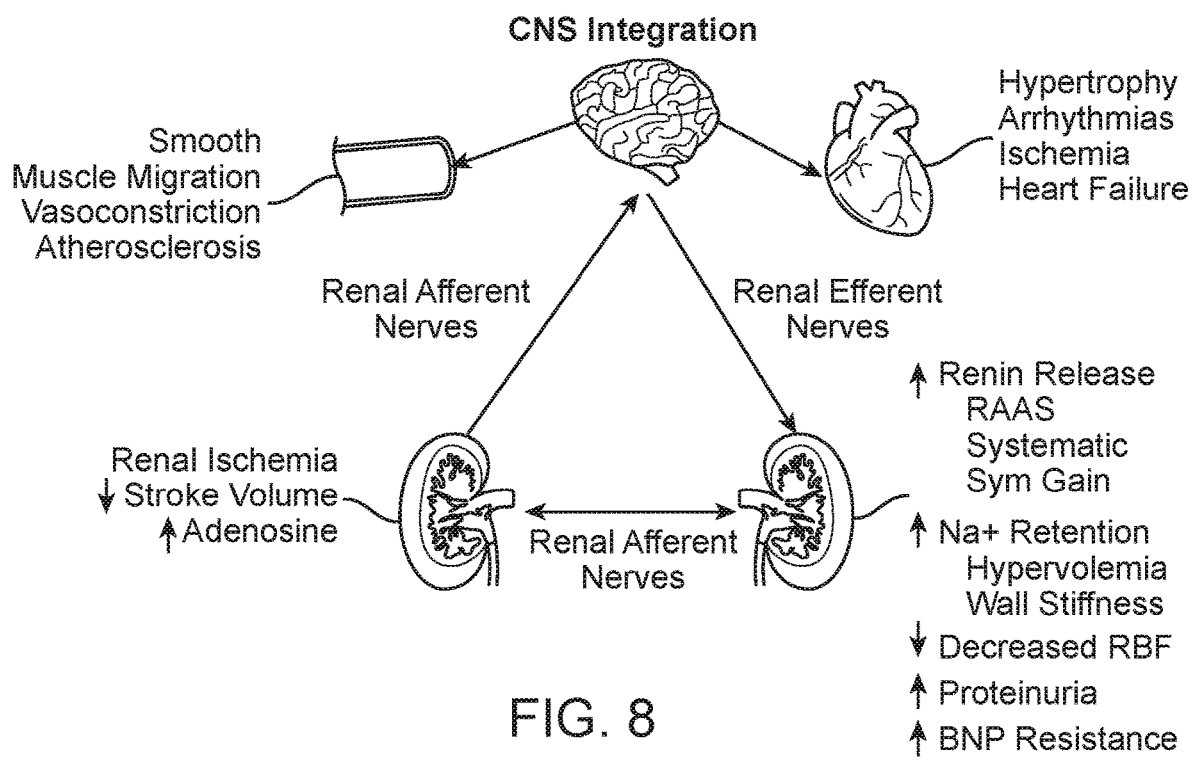
Figures 9, 10:
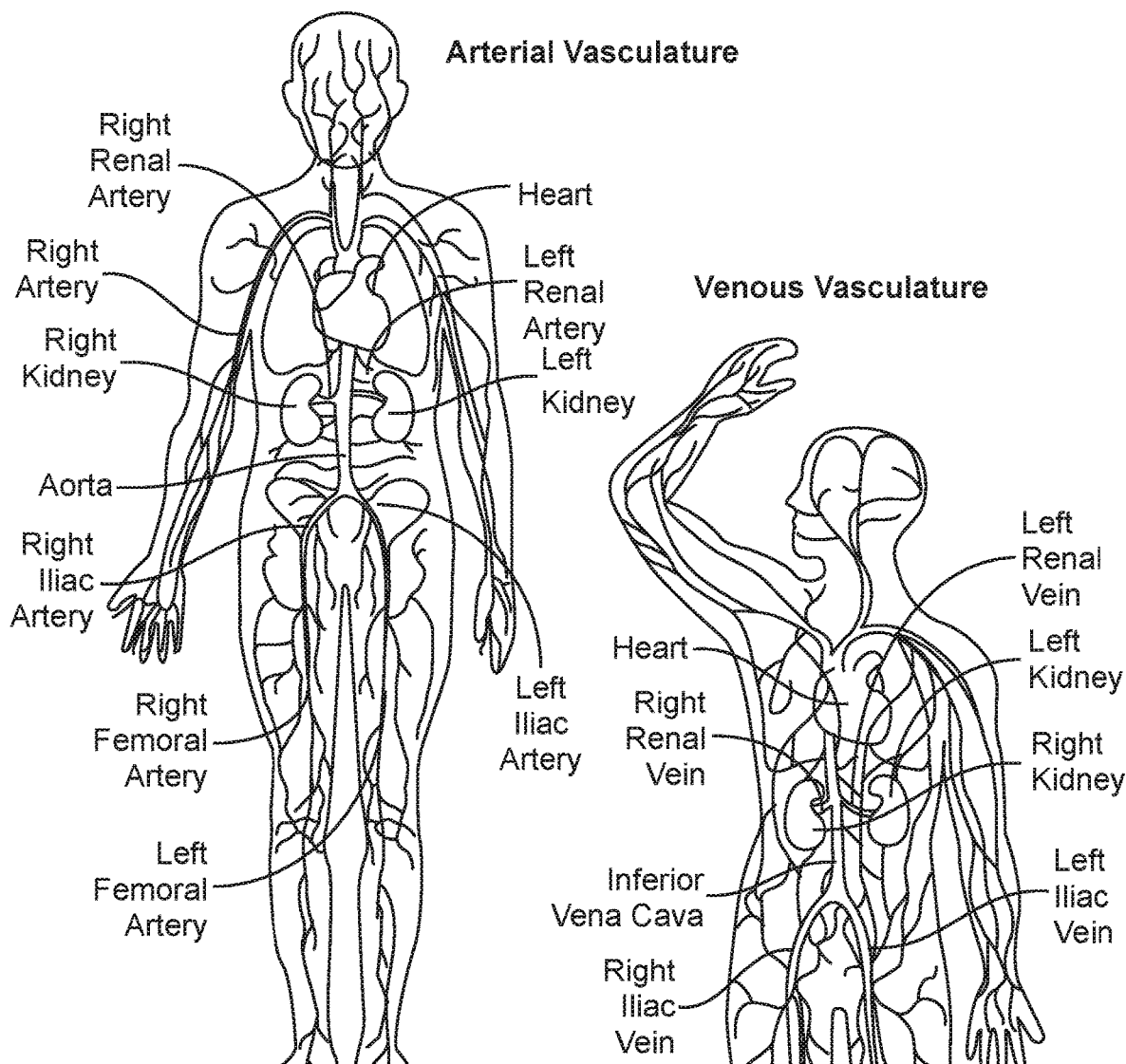
FIGS. 9 and 10 are anatomic views of the arterial vasculature and venous vasculature, respectively, of a human.

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 7 and 8, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 5. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

In accordance with the present technology, neuromodulation of a left and/or right renal plexus (RP), which is intimately associated with a left and/or right renal artery, may be achieved through intravascular access. As FIG. 21 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 22 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for assessing efficacy of renal neuromodulation therapy, the method comprising:
    positioning a neuromodulation catheter having one or more electrodes at a target site within a renal blood vessel of a human patient;
    delivering neuromodulation energy at the target site via the one or more electrodes of the neuromodulation catheter;
    obtaining a measurement related to a dimension of the renal blood vessel including a propagation time of electrical energy delivered through the renal blood vessel via at least one of the one or more electrodes of the neuromodulation catheter;
    comparing the measurement to a baseline measurement related to the dimension of the renal blood vessel including a baseline measurement of the propagation time of electrical energy delivered through the renal blood vessel; and
    assessing efficacy of the renal neuromodulation therapy based, at least in part, on the comparison.

2. The method of claim 1 wherein comparing the measurement to the baseline measurement includes determining a percentage reduction in a diameter of the renal blood vessel.

3. The method of claim 1 wherein obtaining the measurement related to the dimension of the renal blood vessel includes (a) driving electrical signals from at least one of the electrodes through the renal blood vessel and (b) detecting the electrical signals at the one or more electrodes.

4. The method of claim 1 wherein obtaining the measurement related to the dimension of the renal blood vessel includes:
    generating the electrical energy at a first electrode of the one or more electrodes;
    detecting the electrical energy at a second electrode of the one or more electrodes, wherein the second electrode is spaced apart from the first electrode; and
    determining a time difference between generation and detection of the electrical energy.

5. The method of claim 4 wherein the first and second electrodes are located about 90 degrees apart relative to an inner surface of the renal blood vessel.

6. The method of claim 4 wherein the first and second electrodes are located about 180 degrees apart relative to an inner surface of the renal blood vessel.

7. The method of claim 1 wherein obtaining the measurement related to the dimension of the renal blood vessel includes:
    generating and detecting the electrical energy at the same electrode of the one or more electrodes; and
    determining a time difference between generation and detection of the electrical energy.

8. The method of claim 1 wherein the one or more electrodes are disposed on a distal portion of the neuromodulation catheter, and wherein the method further comprises:
    transforming the neuromodulation catheter between a low-profile delivery arrangement and a deployed spiral shape such that at least one of the one or more electrodes contacts an inner surface of the renal blood vessel, and
    wherein delivering neuromodulation energy at the target site includes delivering neuromodulation energy from the at least one of the one or more electrodes.

9. The method of claim 1, further comprising, before delivering neuromodulation energy at the target site, obtaining the baseline measurement related to a diameter of the renal blood vessel via at least one of the one or more electrodes of the neuromodulation catheter.

10. The method of claim 1, further comprising:
when the assessed efficacy is less than a predetermined threshold, delivering additional neuromodulation energy at the target site via the one or more electrodes of the neuromodulation catheter; and
when the assessed efficacy is greater than or equal to the predetermined threshold, moving the neuromodulation catheter from the target site.

11. A neuromodulation system, comprising:
a neuromodulation catheter having a proximal portion and a distal portion, wherein the distal portion is configured to (a) deliver neuromodulation energy at a target site in a renal blood vessel of a human patient and (b) detect one or more measurements related to a dimension of the renal blood vessel including a propagation time of electrical energy delivered through the renal blood vessel; and
a controller configured to be communicatively coupled to the neuromodulation catheter and configured to:
receive the one or more measurements from the neuromodulation catheter;
compare the one or more measurements to a baseline measurement related to the dimension of the renal blood vessel including a baseline measurement of the propagation time of the electrical energy delivered through the renal blood vessel; and
based on the comparison, determine a reduction in the dimension of the renal blood vessel resulting from the neuromodulation energy delivered via the neuromodulation catheter.

12. The system of claim 11 wherein the determined reduction in the dimension of the renal blood vessel is a percentage reduction in a diameter of the renal blood vessel.

13. The system of claim 11 wherein the distal portion of the neuromodulation catheter includes a plurality of electrodes configured to deliver the neuromodulation energy.

14. The system of claim 11 wherein the neuromodulation catheter includes a fiber Bragg grating positioned proximate to the target site in the renal blood vessel.

15. The system of claim 11 wherein the controller is further configured to provide an indication to an operator regarding efficacy of the delivered neuromodulation energy.

16. A method for assessing efficacy of neuromodulation therapy, the method comprising:
positioning a neuromodulation catheter having one or more electrodes at a target site within a renal artery of a human patient;
obtaining a first measurement related to a diameter of the renal artery including a first propagation time of an electrical signal delivered through the renal artery via the one or more electrodes of the neuromodulation catheter;
delivering neuromodulation energy at the target site via the one or more electrodes of the neuromodulation catheter;
obtaining a second measurement related to the diameter of the renal artery including a second propagation time of a second electrical signal delivered through the renal artery via the one or more electrodes of the neuromodulation catheter; and
comparing the first and second measurements to determine a reduction in the diameter of the renal artery resulting from the delivered neuromodulation energy.

17. The method of claim 16, further comprising:
when the reduction in the diameter of the renal artery is less than a predetermined threshold, delivering additional neuromodulation energy at the target site via the one or more electrodes of the neuromodulation catheter; and
when the reduction in the diameter of the renal artery is greater than or equal to the predetermined threshold, moving the neuromodulation catheter from the target site.

18. The method of claim 16 wherein the first and second measurements are average values over a plurality of measurements.

* * * * *